US008594354B2

(12) United States Patent
Klinkby et al.

(10) Patent No.: US 8,594,354 B2
(45) Date of Patent: Nov. 26, 2013

(54) HEARING AID AND METHOD OF ESTIMATING DYNAMIC GAIN LIMITATION IN A HEARING AID

(75) Inventors: Kristian Tjalfe Klinkby, Vaerloese (DK); Peter Magnus Noergaard, Frederiksberg (DK); Helge Pontoppidan Föh, Stenloese (DK)

(73) Assignee: Widex A/S, Lynge (DK)

( * ) Notice: Subject to any disclaimer, the term of this patent is extended or adjusted under 35 U.S.C. 154(b) by 1405 days.

(21) Appl. No.: 12/240,176

(22) Filed: Sep. 29, 2008

(65) Prior Publication Data

US 2009/0067654 A1 Mar. 12, 2009

Related U.S. Application Data

(63) Continuation-in-part of application No. PCT/EP2006/061215, filed on Mar. 31, 2006.

(51) Int. Cl.

| | |
|---|---|
| ***H04R 25/00*** | (2006.01) |
| *G10K 11/16* | (2006.01) |
| *A61F 11/06* | (2006.01) |
| *H03B 29/00* | (2006.01) |

(52) U.S. Cl.

USPC ......... 381/318; 381/71.1; 381/71.6; 381/312; 381/317

(58) Field of Classification Search

USPC ................................ 381/71.1, 71.6, 317, 318

See application file for complete search history.

(56) References Cited

U.S. PATENT DOCUMENTS

2002/0057814 A1* 5/2002 Kaulberg ...................... 381/312

FOREIGN PATENT DOCUMENTS

| | | | |
|---|---|---|---|
| DE | 10159928 | A1 | 5/2003 |
| EP | 1191814 | A1 | 3/2002 |
| EP | 1471765 | A2 | 10/2004 |
| JP | 63001296 | A * | 1/1988 |
| WO | 9409604 | A1 | 4/1994 |
| WO | 0225996 | A1 | 3/2002 |
| WO | 2005096670 | A1 | 10/2005 |

OTHER PUBLICATIONS

Japanese Office Action for Japanese Application No. 2009-501865 dated Sep. 6, 2011.

* cited by examiner

*Primary Examiner* — Duc Nguyen
*Assistant Examiner* — Matthew Eason
(74) *Attorney, Agent, or Firm* — Sughrue Mion, PLLC

(57) ABSTRACT

There is presented a hearing aid that comprises an input transducer for transforming an acoustic input signal into an electrical input signal, a compressor for generating an electrical output signal from the electrical input signal, an output transducer for transforming the electrical output signal into an acoustic output signal, an autocorrelation estimator for calculating an autocorrelation estimate of the electrical input signal, and an acoustic loop gain estimator for determining a dynamic gain limit from the autocorrelation estimate and an instantaneous gain level of the signal processor. The invention further provides a method of adjusting signal path gain in a hearing aid, and a system for providing increased stability in a hearing aid.

21 Claims, 4 Drawing Sheets

HEARING AID AND METHOD OF ESTIMATING DYNAMIC GAIN LIMITATION IN A HEARING AID

RELATED APPLICATIONS

The present application is a continuation-in-part of application no. PCT/EP2006/061215 filed on Mar. 31, 2006 and published as WO-A1-2007112777, the contents of which are incorporated herein by reference.

BACKGROUND OF THE INVENTION

1. Field of the Invention

The present invention relates to the field of hearing aids. The invention more specifically, relates to hearing aids utilizing gain-limitation. The invention, more particularly relates to hearing aids having means for estimating the acoustic loop gain and, still more particularly, relates to hearing aids further incorporating gain limitation in order to reduce disturbances due to acoustic feedback, and respective systems and methods thereof. In addition the invention relates to a system exploiting the increase in gain margin due to the utilization of feedback cancellation techniques by permitting larger signal path gain in the hearing aid.

2. Description of the Related Art

It is a general object in hearing aid design to establish the maximum possible amount of gain with which an acoustic input signal may be amplified to produce a hearing loss compensation signal without the appearance of acoustic feedback or other acoustic disturbances.

WO-A-94/09604 discloses a hearing aid with digital, electronic compensation for acoustic feedback, which comprises a compensation circuit. The circuit monitors the loop gain and regulates the hearing aid amplification so that the loop gain is less than a constant K. An adaptive filter operates to minimize the correlation between input and output from the hearing aid and may be used to give a measure of the attenuation in the acoustic feedback path by deriving gain and phase characteristics from a feedback cancellation filter.

WO-A-02/25996 discloses a hearing aid with an adaptive filter for suppression of acoustic feedback. The adaptive filter may be used as an independent measuring system to estimate the acoustic feedback signal without distortion of the processed acoustic input signal.

Data derived from the adaptive filter may be used to determine loop gain, which may be utilized to set an upper limit on the applicable gain that may be used in each of multiple evaluated frequency bands.

It is further known that a large autocorrelation measurement may indicate feedback oscillation. Accordingly, feedback detectors that rely on autocorrelation measurements have been suggested in the prior art.

However, neither of these documents discloses how in situations with high, and increasing, autocorrelation, a gain limit could be identified in situations where the known solutions, e.g. measuring gain in the acoustic feedback path with an adaptive feedback cancellation filter, cannot be relied upon.

The most common technique to alleviate feedback oscillations is gain-reduction. Managing feedback by gain reduction is in particular a problem in linear hearing aids. Most linear hearing aids are adapted for greater gain in the high frequencies, where the hearing deficiency tends to be more profound. Unfortunately, the typical feedback path also provides less attenuation at high frequencies than at low frequencies. Therefore, the risk of audible feedback is highest in the higher frequency range. One common method to control feedback is to lower the high frequency gain of the hearing aid. However, speech intelligibility may suffer as a consequence.

Therefore, disturbances in the output signal of a hearing aid as well as instability and limited available gain are still challenges in today's hearing aid design.

Thus, there is a need for improved hearing aids as well as improved techniques for utilizing gain-limitation in hearing aids.

SUMMARY OF THE INVENTION

It is therefore an object of the present invention to provide hearing aids and methods of processing signals in a hearing aid taking in particular the mentioned requirements and drawbacks of the prior art into account.

It is in particular an object of the present invention to provide a hearing aid and a respective method incorporating a stabilized closed loop system capable of managing a situation where the hearing aid is exposed to a non-stationary environment.

It is a further object of the present invention to provide a hearing aid and a respective method providing an increased possible amplification in the signal processor of a hearing aid wherein the closed loop gain is decreased by cancellation techniques.

It is another object of the present invention to provide a hearing aid and a respective method capable of estimating a dynamic gain limit of the signal processor.

It has been established that information on the attenuation in the acoustic feedback path may also be derived from the compressor that is incorporated in hearing aids which operates with non-linear amplification—known as hearing aids with dynamic compression.

According to a first aspect of the present invention, there is provided a hearing aid comprising: an input transducer for transforming an acoustic input signal into an electrical input signal; a compressor for generating an electrical output signal from said electrical input signal; an output transducer for transforming said electrical output signal into an acoustic output signal; an autocorrelation estimator for calculating a level of autocorrelation of said current electrical input signal; and an acoustic loop gain estimator for determining a dynamic gain limit from the calculated level of autocorrelation and an instantaneous gain level of said compressor.

The hearing aid with the acoustic loop gain estimator uses the autocorrelation estimate and instantaneous compressor gain level from the signal processor to estimate a dynamic gain limit and, thus, enables it to utilize the compressor gain setting as a measure for the gain limit value in situations with high and/or increasing autocorrelation of the input signal.

The compressor of the hearing aid according to the present invention is capable of providing less gain at higher input levels since the gain is adjusted in dependency of the input level. In case of a feedback tone, the compressor automatically sets in to control the level of the signal. Generally, however, the compressor will not remove the feedback tone. It will only stabilize the tone around the stability border. The settling gain level is then equivalent to the acoustic loop amplification, under the assumption that all other system components apply unity gain. This feature is utilized in the current invention by using the instantaneous compressor gain level when estimating the dynamic gain limit. In systems wherein gain is distributed among other components, the instantaneous gain stability level will include the contribution from those, possibly non-stationary, elements. However, for the purpose of measuring which instantaneous gain level that may be applied, it is sufficient to study the compressor gain level, given that this calculation is performed much more often than other gain adjustments.

Besides the continuous compressor gain levels the invention uses estimates of autocorrelation in the signal. Autocorrelation is caused by predictability in the signal. Periodic signals, like harmonic oscillations, have substantial autocorrelation that can be detected by methods known to the skilled person. Accordingly, a feedback tone will have large autocorrelation. So, by detecting a critically large autocorrelation estimate and establishing the instantaneous compressor gain level, the invention can estimate an acoustic loop gain and apply a lower gain limit value to ensure stability. Knowing the gain level in the compressor and the fact that closed loop gain is unity in that situation, attenuation in the feedback path can be calculated simply by reversing the sign of the gain level in the dB-domain. The lower estimated gain limit may have a value which is just a few dB below the estimated acoustic loop gain. With that, the invention can also cope with a potential error in other acoustic loop gain estimating systems, wherein signals with large autocorrelation, like music for instance, may cause those systems to fail, since it is possible, according to the present invention, to limit the amount of gain restriction relative to the instantaneous compressor gain level. This limit should be chosen large enough to remove the feedback tone and small enough to prevent gain modulation in case of auto correlated input signals. Normally a couple of dB gain reduction is sufficient.

Contrarily, according to another aspect of the present invention, if a decrease of autocorrelation below a critical value has been detected, the acoustic loop gain estimator arranges for a gradual release of the gain limitation until the compressor again controls the gain setting.

According to a second aspect of the present invention, there is provided a hearing aid comprising: an input transducer for transforming an acoustic input signal into an electrical input signal; a signal processor for generating an electrical output signal from a feedback compensated input signal; an output transducer for transforming said electrical output signal into an acoustic output signal; an adaptive filter for estimating an acoustic feedback signal from said electrical output signal and said feedback compensated input signal; a combiner for generating said feedback compensated input signal by combining said estimated acoustic feedback signal with said electrical input signal; an autocorrelation estimator for generating a level of autocorrelation of said feedback compensated input signal; and an acoustic loop gain estimator for determining a dynamic gain limit from said calculated level of autocorrelation and an instantaneous gain level of said signal processor.

The hearing aid according to this aspect provides an adaptive filter that enables it to suppress the time varying acoustic feedback and, thus, increases the possible amplification in the signal processor if the closed loop gain is decreased below unity. Since the adaptive filter increases the stability margin, the invention can increase the gain limit.

According to another aspect of the present invention, the compressor time constants are shorter than the cancellation systems time-window so that gain-adjustment is faster than adaptation of the feedback compensation. Thus, the hearing aid according to the present invention has the ability to react fast on sudden changes in the environment and assure uninterrupted stability. Meanwhile the adaptive filter has time to slowly adjust to the new environment thereby increasing the stability margin. Concurrently the invention increases the gain limit. Methods for suppressing the time varying acoustic feedback with an adaptive filter are described, for example, in WO 02/25996 A1.

According to a third aspect of the present invention, there is provided a method of adjusting signal path gain in a hearing aid, comprising the steps of: transforming an acoustic input signal into an electrical input signal; generating an electrical output signal by amplifying said electrical input signal with a compressor gain provided by a compressor of said hearing aid depending on the level of said electrical input signal; transforming said electrical output signal into an acoustic output signal; calculating a level of autocorrelation of said current electrical input signal; and estimating a dynamic gain limit based on said calculated level of autocorrelation and the instantaneous compressor gain level for controlling said compressor gain.

It may be seen as a true advantage that the hearing aids, systems and methods according to the present invention provide the ability to dynamically adjust the amount of gain that the hearing aid or system may apply at any given instance.

According to an embodiment of the present invention the hearing aid is able to adjust the possible maximum gain limit from the instantaneous gain level and in dependence of the currently calculated autocorrelation estimate. This provides an alternative way of identifying at which gain limit value a hearing aid is able to operate without the occurrence of feedback resonance.

The invention, according to a fourth aspect, provides a computer program comprising executable program code which, when executed on a computer, executes a method of adjusting signal path gain in a hearing aid, comprising the steps of: transforming an acoustic input signal into an electrical input signal; generating an electrical output signal by amplifying said electrical input signal with a compressor gain provided by a compressor of said hearing aid depending on the level of said electrical input signal; transforming said electrical output signal into an acoustic output signal; calculating a level of autocorrelation of said current electrical input signal; and estimating a dynamic gain limit based on said calculated level of autocorrelation and the instantaneous compressor gain level for controlling said compressor gain.

Further specific variations of the invention are defined by the further dependent claims.

Other aspects and advantages of the present invention will become more apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

When describing the invention according to embodiments thereof, terms will be used which are described as follows:

Maxgain or maximum gain limit: the upper limit to gain that can be applied without the occurrence of feedback resonance. Some safety margin (e.g. 12 dB) may be subtracted from the calculated limit.

Compressor: a device commonly utilized in modern hearing aids, which operates to compress the dynamic range of the input signals. Useful for treatment of presbyscusis (loss of dynamic range due to haircell-loss). Compressing hearing aids often apply expansion for low level signals, in order to suppress microphone noise. The compressor may also incorporate a soft-limiter adapted to limit maximum output level at safe or comfortable levels. The compressor has a non-linear gain characteristic and, thus, is capable of providing less gain at higher input levels and more gain at lower input levels. Hearing aids employing a compressor in the signal processor are often referred to as non-linear gain or compressing hearing aids.

Closed loop system: comprises an input transducer or microphone, a signal processor amplifying the input signal, an output transducer or receiver and an acoustic feedback path. In stationary environments the stabilization is obtained by limiting the amplification in the signal processor below a gain limit value. In a non-stationary environment stabilization is obtained by reducing the gain limit in the signal processor if the closed loop gain is approaching unity, i.e. 0 dB loop gain, when the environment changes.

Closed loop gain: A concept known from e.g. control systems theory. In a system comprising a forward path wherein gain is A and a feedback path wherein gain is B, wherein the input signal (I) is amplified in the forward path in order to generate the output signal (O) and wherein the signal in the feedback path is added to the input signal, closed loop gain is O/I=A/(1+AB). In such a system, it is also common to refer to the open loop gain AB. In a marginally stable system open loop gain is −1.

Acoustic loop gain: The inverse, in the logarithmic domain, of the gain in the acoustic feedback path (B in the example above).

Signal processor: The component that compensates the hearing loss, in a general sense. Often, the main amplifying element comprises a compressor. The processor may include systems for noise reduction and/or speech enhancement. Even though directional processing may be provided in the hearing aid front-end, such spatial filtering should be considered as comprised by the processing in the signal processor.

Figure 1:
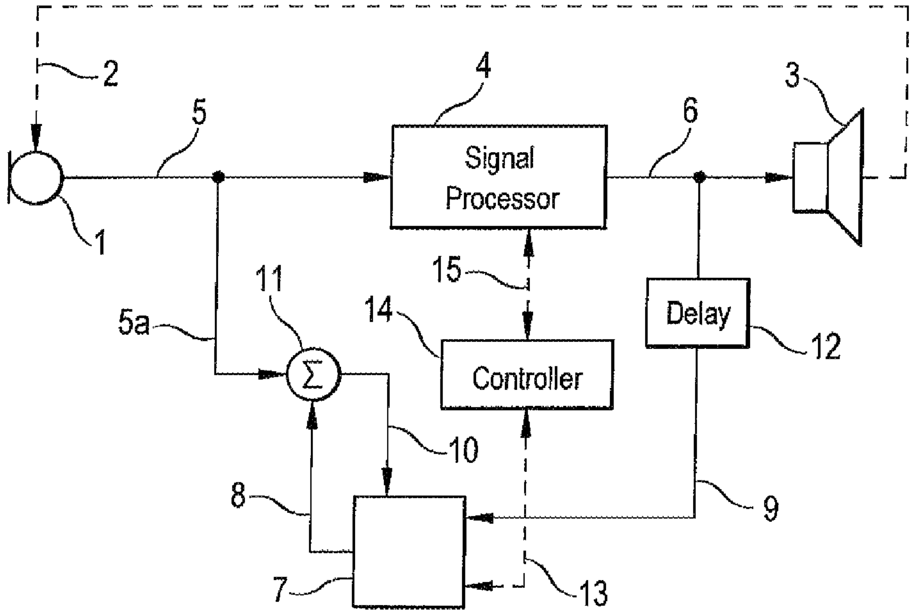
PRIOR ART FIG. 1
FIG. 1 depicts a schematic block diagram of a hearing aid according to the prior art.

With reference to FIG. 1 it is explained in some detail how an estimate of gain in the acoustic feedback path may be determined in the prior art. The microphone 1 is subject to acoustic feedback propagating along feedback path 2 from the receiver 3. In addition to the desired signal, this feedback signal is transmitted to the signal processor 4 as input signal 5. After processing in the signal processor 4 the processor output signal 6 is transmitted to the receiver 3 for conversion to an acoustic output signal. An adaptive filter 7 operates to minimize cross-correlation between input 5*a* and output 6, and consequently generates an estimate 8 of the acoustic feedback signal. By analysis of the transfer function of this filter an estimate of gain in the feedback path can be obtained. The adaptive filter operates to minimize the so-called error signal 10 ($\epsilon$) which is generated by subtracting the estimate 8 from the input signal 5*a* in a subtractor 11.

Figure 2:
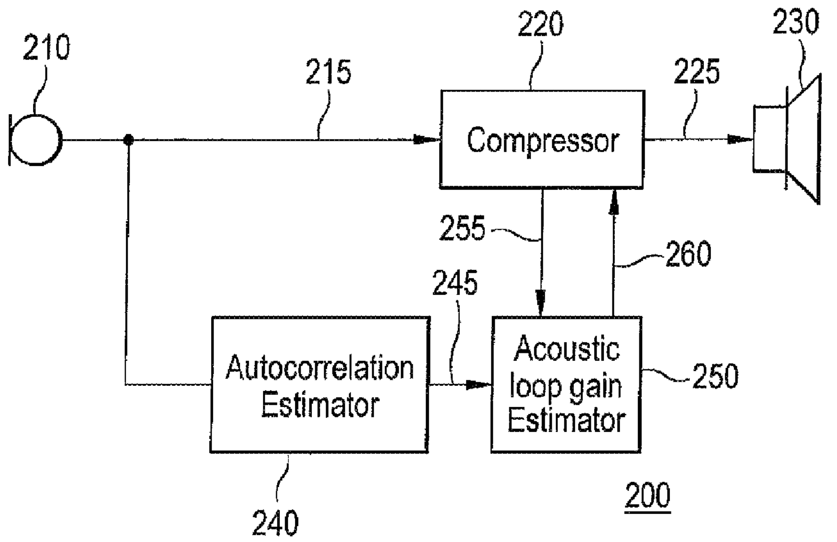
FIG. 2 depicts a schematic block diagram of a hearing aid according to a first embodiment of the present invention.

Reference is now made to FIG. 2, which shows a hearing aid 200 according to the first embodiment of the present invention.

The hearing aid comprises an input transducer or microphone 210 transforming an acoustic input signal into an electrical input signal 215, and an A/D-converter (not shown) for sampling and digitizing the analogue electrical signal. The converted electrical input signal is fed into a compressor 220 generating an electrical output signal 225 by applying a compressor gain in order to produce an output signal that is hearing loss compensated to the user requirements. The compressor gain characteristic is non-linear to provide more gain at low input signal levels and less gain at high signal levels. The signal path further comprises an output transducer 230 like a loudspeaker or receiver transforming the electrical output signal into an acoustic output signal.

The hearing aid further comprises an autocorrelation estimator 240 calculating an autocorrelation estimate 245 of the received electrical input signal 215. The autocorrelation estimate is feed to an acoustic loop gain estimator 250, wherein a dynamic gain limit 260 is determined, from an instantaneous gain level 255 applied by the compressor 220, in dependency of the autocorrelation estimate. The gain limit is then used by the compressor to limit the signal path gain in order to secure overall signal stability. Several methods for estimation of autocorrelation are known in the art.

The hearing aid according to the first embodiment is a compressing hearing aid wherein feedback elimination is provided by evaluating signal autocorrelation, and, once autocorrelation at or above a critical value is detected by the autocorrelation estimator 240, by the acoustic loop gain estimator 250 limiting the gain limit at the settling value of the compressor gain instantaneously received from the compressor 220.

The acoustic loop gain estimator 250 is adapted to generate an upper processor gain limit or gain limit by determining the acoustic loop gain in case of instability. Instability is detected by the autocorrelation estimator 240. The acoustic loop gain is estimated by determining the instantaneous compressor gain level, utilizing the fact that the open loop gain is equal to −1 in situations with instability. The instantaneous compressor gain level 255 is read from the compressor. The gain limit is then adjusted according to the estimated acoustic loop gain and fed to the compressor as upper processor gain limit 260 to limit the signal path gain applied to the input signal when generating the output signal of the processor.

According to an embodiment of the invention, a safety margin is established by subtraction of a constant, $M_{dB}$, e.g. 3 dB, from the estimated dynamic gain limit (the estimated acoustic loop gain—in the dB-domain).

Figure 3:
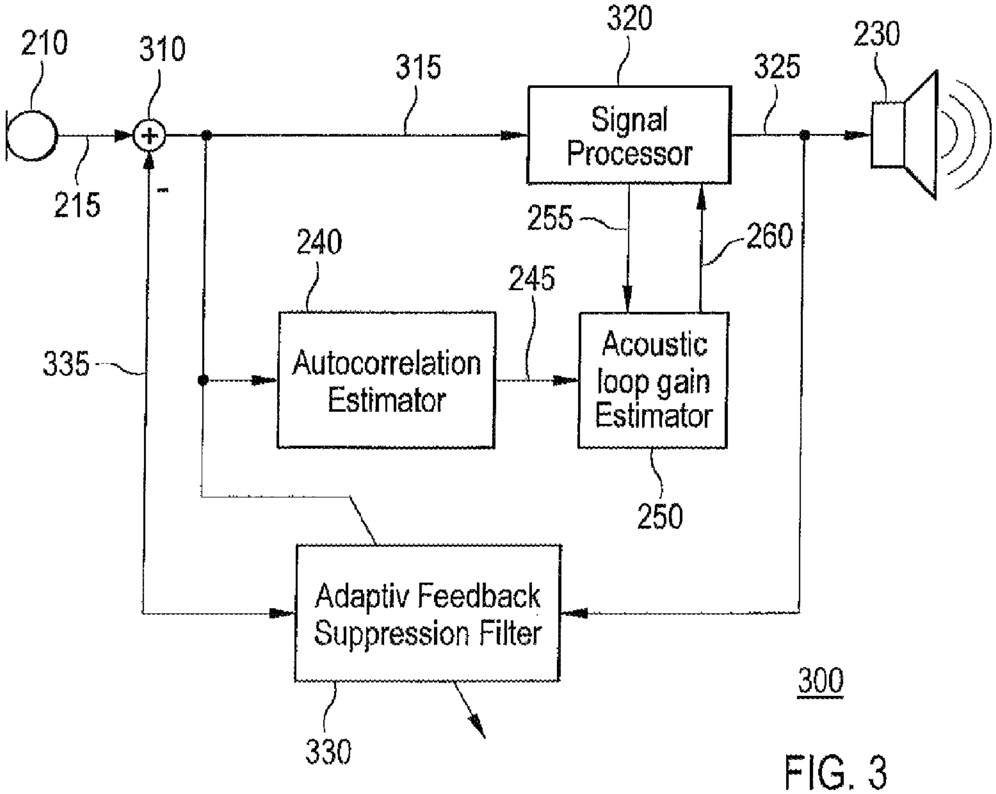
FIG. 3 depicts a schematic block diagram of a hearing aid according to a second embodiment of the present invention.

FIG. 3 shows a block diagram of a hearing aid 300 of the second embodiment of a hearing aid according to the present invention. This is a compressing hearing aid 300 wherein adaptive feedback cancellation means 330 is applied in order to eliminate, or reduce, feedback resonance, and wherein signal autocorrelation is evaluated for the feedback compensated signal. In this hearing aid, once autocorrelation at or above a critical value is detected, a gain limit at the settling value of the compressor gain is provided. The effect of feedback cancellation may be taken as an advantage enabling to increase the stability margin of the hearing aid.

The signal path of the hearing aid comprises an input transducer 210 or microphone transforming an acoustic input signal into an analogue electrical input signal, and an A/D-converter (not shown) for sampling and digitizing the analogue electrical signal into a digital, electrical input signal 215 to be further processed by the system. This signal 215 is compensated for the acoustic feedback by subtracting an estimate of the acoustic feedback signal 335 from the electrical input signal 215 in a combiner 310 to generate a feedback compensated input signal 315. The feedback compensated input signal 315 is fed into a signal processor 320 generating an amplified electrical output signal 325.

According to an embodiment of the invention, the amplification characteristic of the signal processor is non-linear, e.g. it shows compression characteristics providing more gain at low signal levels and less gain at high signal levels, as is well known in the art.

The signal path further comprises an output transducer 230 like a loudspeaker or receiver transforming the electrical output signal 325 into an acoustic output signal. According to an embodiment, the adaptive feedback cancellation means is implemented as an adaptive feedback suppression filter 330 which uses the output signal 325 and the feedback compensated input signal 315 to estimate the acoustic feedback signal 335. The autocorrelation estimator 240 derives its estimate on the basis of the compensated input signal 315. So if the adaptive suppression filter removes correlation between the output signal 325 and the electrical input signal 215, this correlation will not be part of the autocorrelation estimate. This is in particular intended according to an embodiment of the invention, according to which the acoustic loop gain estimator 250 will not dictate a lower gain limit when the adaptive feedback suppression filter 330 has increased the stability margin by removing correlation between the output and input signals.

The adaptive feedback suppression filter 330 analyzes cross-correlation between the input signal 215 and the signal processor output signal 325 and generates an estimate of the acoustic feedback signal 335. By analysis of the transfer function of the adaptive filter 330, an estimate of the gain in the acoustic feedback path can be obtained. The adaptive filter 330 operates to minimize the feedback compensated input signal 315, which is generated by a combiner 310 by subtracting the estimate of the acoustic feedback signal 335 from the input signal 215. The amount of acoustic feedback may be estimated by determination of a parameter like the ratio between the input and output signal of the adaptive filter 330. The way of implementing such filters will be known to the person skilled in the art, e.g. from the disclosure in WO-A-02/25996.

According to an embodiment, the estimated acoustic feedback signal is provided to the signal processor for increasing the gain margin of the signal processor 320. Empirically, the effect of feedback cancellation is an increase in the gain margin in the order of 20 dB. Accordingly, the gain limit safety margin ($M_{dB}$) may be set at e.g. −17 dB (−20 dB on account of cancellation +3 dB on account of the safety margin mentioned in the first embodiment), such that maximum available gain is set 17 dB higher than the gain limit estimation based on the calculation without the adaptive filter.

The present invention further provides a method for adjusting the signal path gain in a hearing aid as will be described in the following with reference to FIG. 4.

Figure 4:
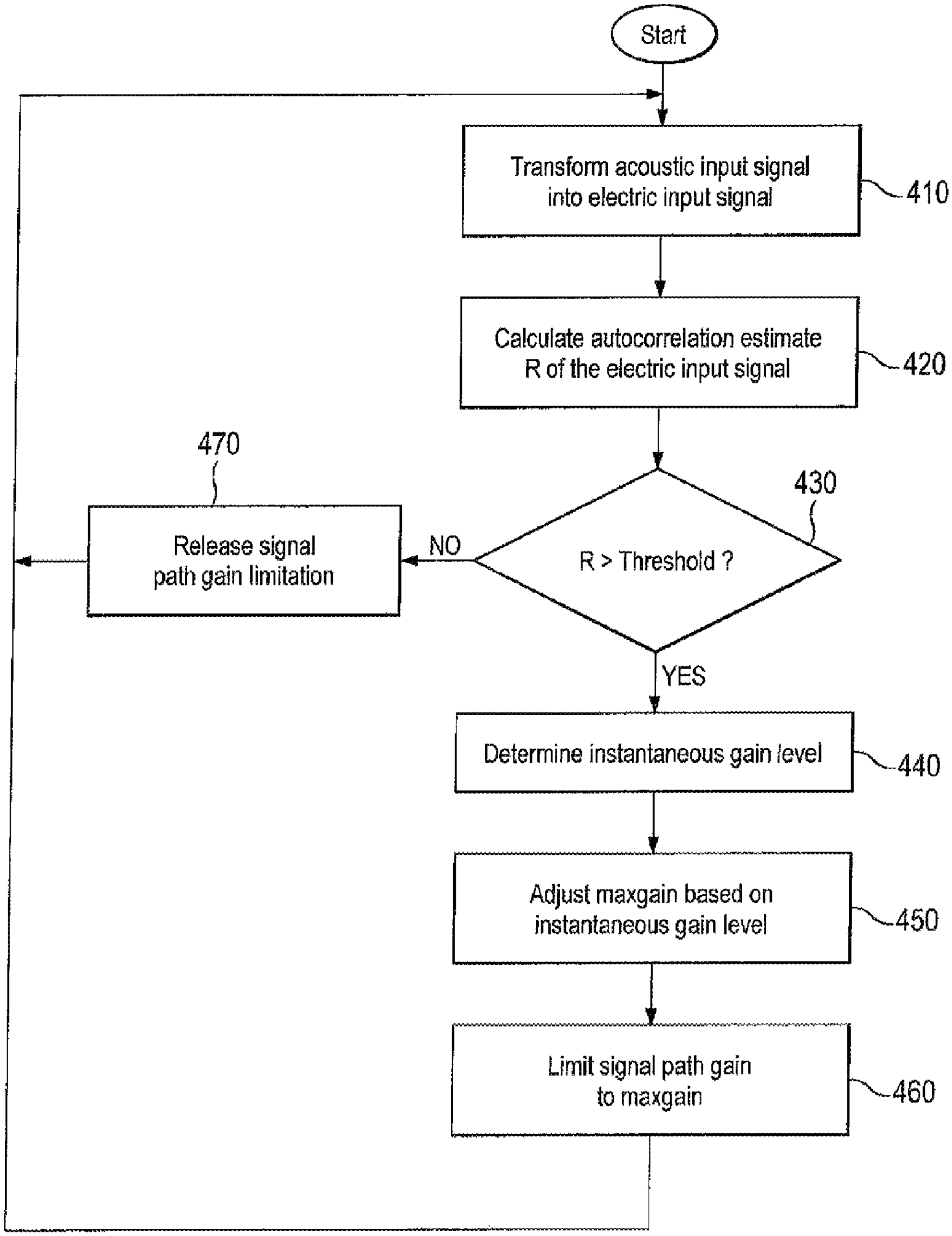
FIG. 4 depicts a flow diagram of a method according to an embodiment of the present invention.

According to the embodiment depicted in FIG. 4, an acoustic input signal is transformed into an electrical input signal by an input transducer in method step 410. Further processing of the input signal by e.g. an A/D-converter is not shown in FIG. 4. In method step 420, an autocorrelation estimate R of the electrical input signal is calculated. The estimate R is then evaluated by, e.g., comparing the estimate R with a threshold as shown in method step 430. If the estimate R is greater than the threshold, the method branches to step 440 wherein the instantaneous gain level is determined. The gain limit is then estimated based on the autocorrelation estimate and the instantaneous gain level in the following steps. Specifically, the gain limit is adjusted based on the determined instantaneous gain level in method step 450 so that the estimated loop gain will be decreased. In method step 460, the signal path gain will then be limited to the adjusted gain limit. Thus, the electrical output signal is generated by amplifying the electrical input signal with a compressor gain limited by the gain limit and depending on the level of the electrical input signal. In order to produce an acoustic output signal, the electrical output signal is transformed into an acoustic output signal.

If the estimate R is below the threshold, the method branches to step 470, wherein the signal path gain limitation is released. In order to avoid "pumping" of the output signal, the gain limit will be released gradually until there is no limitation any more.

Figure 5:
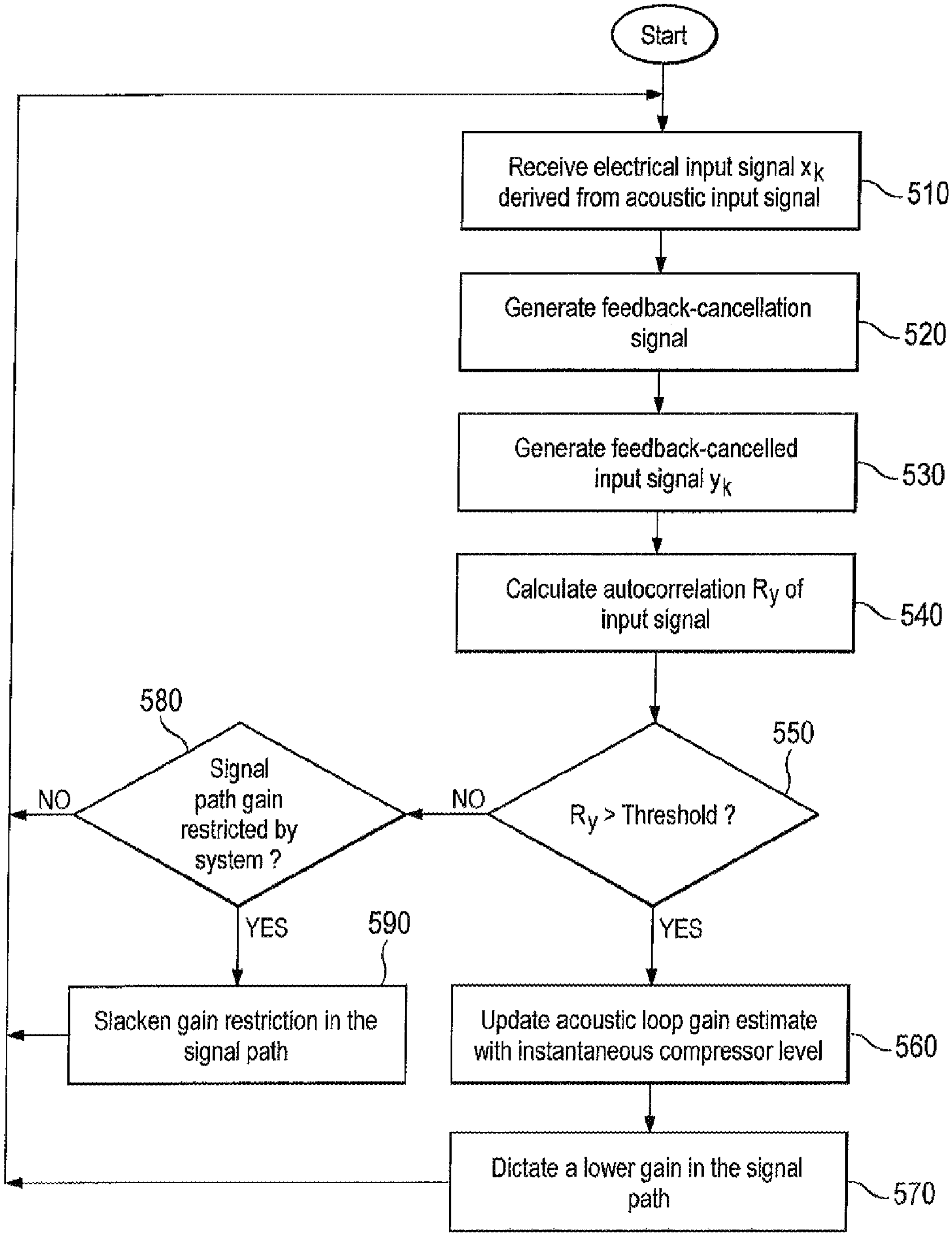
FIG. 5 depicts a flow diagram of a method according to another embodiment of the present invention.

The invention also provides a method for increasing the maxgain in cooperation with the adaptive feedback suppression filter as illustrated by the flowchart of FIG. 5.

The flowchart of FIG. 5 also illustrates how the method according to an embodiment of the present invention is able to reduce acoustic feedback of a hearing aid. The received acoustic input signal is transformed into an electrical input signal $x_k$ by a microphone in method step 510. In a subsequent method step 520 a feedback-cancellation signal is produced by an adaptive filter, which signal is then subtracted from the electrical input signal resulting in feedback-cancelled input signal $y_k$ (step 530). In next step 540 an estimate of the autocorrelation $R_y$ of the feedback-cancelled input signal $y_k$ is calculated. The level of autocorrelation is then compared with a threshold value in method step 550. If the comparison result is positive, that is if the autocorrelation is larger than the given threshold value, the acoustic loop gain estimate is updated with the instantaneous compressor level in method step 560. Subsequently the method will dictate a lower gain limit in method step 570.

If, on the other hand, the autocorrelation is smaller than the given threshold value, in method step 580 the method checks whether it restricts the signal path gain with the dictated maxgain or not. If the outcome is positive, that is if the signal path gain is larger than the dictated maxgain, the method will slacken the gain restriction by increasing the maxgain in method step 590. If the outcome is negative, the method will start all over again.

According to an embodiment of the present invention, in order to reduce "pumping" of the output signal the slackening is implemented by a gradual release of the gain limitation until the compressor again controls the signal path gain setting. According to another embodiment, the pumping may also be avoided by appropriate selection of time constants in the control system.

According to an embodiment, in order to reduce the system load, the maxgain-estimate will be updated less frequently than at full system speed, e.g. at 0.5 ms intervals.

Naturally, more than one system for estimation of maxgain may be applied, e.g. the adaptive estimation systems disclosed in, e.g., WO-A-02/25996, in addition to the other systems explained. In such a system, some kind of decision unit will be provided in order to select which estimate to use or, possibly, decide on utilization of an average estimate.

According to an embodiment, in situations where it is determined, by other measures known to the skilled person, that the estimate of the acoustic loop gain may not be correct, the updating of the maxgain estimates could be halted. Alternatively, another system for determination of gain limit may be applied. An example of such a situation would be the detection, in a multimicrophone hearing aid, of high autocorrelation in both microphone signals. This could be the situation when listening to music. Under the presumption that the time-resolution is such that a difference in autocorrelation in the two microphone signals—which would indicate feedback oscillation in one microphone path—could be detected, this would indicate that, even though autocorrelation is high, no maxgain limitation should be applied.

According to an embodiment, during power-up of the hearing aid, a conservative maxgain value could be maintained until the acoustic loop gain estimation system is fully operative. Alternatively, the threshold level for deciding that autocorrelation is above feedback resonance level may be kept at a relatively low level during this period.

As instability often occurs in a limited narrow frequency range, it is desirable to decrease the gain only in that limited frequency range. Therefore, according to an embodiment, the whole architecture is wholly or partially band-split, i.e. one or more of the adaptive filter (if applicable), the signal processor, the maxgain control system and the autocorrelation system operate in several bands. The skilled person knows how this is to be achieved. The acoustic loop gain is accordingly estimated separately in those bins and the amplification in the signal processor is controlled in identical bins. This way maximum amplification can be assured in a maximum frequency span. Consequently speech intelligibility can be maintained almost unaltered.

According to a further embodiment, the acoustic loop gain estimation is omitted for lower frequency bands, since acoustic feedback rarely occurs in the lower frequency bands.

All appropriate combinations of features described above are to be considered as belonging to the invention, even if they have not been explicitly described in their combination.

According to embodiments of the present invention, hearing aids described herein may be implemented on signal processing devices suitable for the same, such as, e.g., digital signal processors, analogue/digital signal processing systems including field programmable gate arrays (FPGA), standard processors, or application specific signal processors (ASSP or ASIC). Obviously, it is preferred that the whole system is implemented in a single digital component even though some parts could be implemented in other ways—all known to the skilled person.

Hearing aids, methods and devices according to embodiments of the present invention may be implemented in any suitable digital signal processing system. The hearing aids, methods and devices may also be used by, e.g., the audiologist in a fitting session. Methods according to the present invention may also be implemented in a computer program containing executable program code executing methods according to embodiments described herein. If a client-server-environment is used, an embodiment of the present invention comprises a remote server computer which embodies a system according to the present invention and hosts the computer program executing methods according to the present invention. According to another embodiment, a computer program product like a computer readable storage medium, for example, a floppy disk, a memory stick, a CD-ROM, a DVD, a flash memory, or any other suitable storage medium, is provided for storing the computer program according to the present invention.

According to a further embodiment, the program code may be stored in a memory of a digital hearing device or a computer memory and executed by the hearing aid device itself or a processing unit like a CPU thereof or by any other suitable processor or a computer executing a method according to the described embodiments.

Having described and illustrated the principles of the present invention in embodiments thereof, it should be apparent to those skilled in the art that the present invention may be modified in arrangement and detail without departing from such principles. Changes and modifications within the scope of the present invention may be made without departing from the spirit thereof, and the present invention includes all such changes and modifications.

The invention claimed is:

1. A hearing aid comprising:

an input transducer for transforming an acoustic input signal into an electrical input signal;

a compressor for generating an electrical output signal from said electrical input signal;

an output transducer for transforming said electrical output signal into an acoustic output signal;

an autocorrelation estimator for calculating a level of autocorrelation of said current electrical input signal; and an acoustic loop gain estimator for determining a dynamic gain limit from the calculated level of autocorrelation and an instantaneous gain level of said compressor.

2. The hearing aid according to claim 1, further comprising:

a combiner for generating a feedback compensated input signal by combining an estimated acoustic feedback signal with said electrical input signal, and for feeding the feedback compensated input signal as input signal to said compressor and said autocorrelation estimator; and an adaptive filter for estimating said acoustic feedback signal from said electrical output signal and said feedback compensated input signal.

3. The hearing aid according to claim 2, wherein said compressor has a gain-adjustment rate which is faster than the adaptation rate of said adaptive filter suppressing the time-varying acoustic feedback.

4. A hearing aid comprising:

an input transducer for transforming an acoustic input signal into an electrical input signal;

a signal processor for generating an electrical output signal from a feedback compensated input signal;

an output transducer for transforming said electrical output signal into an acoustic output signal;

an adaptive filter for estimating an acoustic feedback signal from said electrical output signal and said feedback compensated input signal;

a combiner for generating said feedback compensated input signal by combining said estimated acoustic feedback signal with said electrical input signal;

an autocorrelation estimator for generating a level of autocorrelation of said feedback compensated input signal; and an acoustic loop gain estimator for determining a dynamic gain limit from said calculated level of autocorrelation and an instantaneous gain level of said signal processor.

5. The hearing aid according to claim 4, wherein said acoustic loop gain estimator is further adapted to determine said dynamic gain limit based on said estimated acoustic feedback signal.

6. The hearing aid according to claim 4, wherein said acoustic loop gain estimator is further adapted to evaluate the value of said level of autocorrelation; and, if said level of autocorrelation is detected at or above a threshold value, said acoustic loop gain estimator is operated to determine said instantaneous gain level, to update the acoustic loop gain estimate with said instantaneous signal processor gain level, to adjust said dynamic gain limit, and to limit said signal path gain by said dynamic gain limit.

7. The hearing aid according to claim 4, wherein said acoustic loop gain estimator is adapted to further adjust said dynamic gain limit by subtracting a safety margin from said dynamic gain limit.

8. The hearing aid according to claim 4, wherein said acoustic loop gain estimator is further adapted, to release the limitation of said signal path gain in the event said level of autocorrelation is detected below said threshold value.

9. The hearing aid according to claim 8, wherein said acoustic loop gain estimator is further adapted to check whether said signal path gain is restricted by said dynamic gain limit and, if said signal path gain is restricted, to slack said gain limitation by increasing said dynamic gain limit.

10. The hearing aid according to claim 4, further comprising a band-split filter for converting said electrical input signal into band-split electrical input signals of a plurality of frequency bands and wherein said hearing aid is further adapted to process said band-split electrical input signals in each of said frequency bands independently.

11. A method of adjusting signal path gain in a hearing aid, comprising the steps of:

transforming an acoustic input signal into an electrical input signal;

generating an electrical output signal by amplifying said electrical input signal with a compressor gain provided by a compressor of said hearing aid depending on the level of said electrical input signal;

transforming said electrical output signal into an acoustic output signal;

calculating a level of autocorrelation of said current electrical input signal; and estimating a dynamic gain limit based on said calculated level of autocorrelation and the instantaneous compressor gain level for controlling said compressor gain.

12. The method according to claim 11, wherein said step of estimating said dynamic gain limit further comprises:

evaluating the value of said level of autocorrelation; detecting whether said level of autocorrelation is at or above a threshold value, and in the affirmative, proceeding with determining said instantaneous compressor gain level;

updating the acoustic loop gain with said instantaneous compressor gain level;

adjusting said dynamic gain limit; and limiting said signal path gain by said dynamic gain limit.

13. The method according to claim 12, wherein the step of adjusting said dynamic gain limit comprises decreasing said dynamic gain limit.

14. The method according to claim 12, wherein the step of adjusting said dynamic gain limit further comprises subtracting a safety margin from said dynamic gain limit.

15. The method according to claim 11, wherein said step of estimating said dynamic gain limit further comprises detecting whether said level of autocorrelation is detected below said threshold value, and in the affirmative releasing the limitation of said signal path gain.

16. The method according to claim 15, wherein said releasing step comprises:

checking whether said signal path gain is restricted by said dynamic gain limit, and in the affirmative slacking said gain limitation by increasing said dynamic gain limit.

17. The method according to claim 11, further comprising:

estimating an acoustic feedback signal from said electrical output signal;

generating a feedback-compensated input signal; and generating said electrical output signal and said level of autocorrelation from said feedback-compensated input signal.

18. The method according to claim 17, wherein said acoustic feedback signal is estimated by an adaptive filter using said feedback-compensated input signal.

19. The method according to claim 11, further comprising the step of converting said electrical input signal into band-split electrical input signals of a plurality of frequency bands and wherein said method is further carried out in each of said frequency bands independently.

20. A computer program comprising executable program code tangibly embodied on a non-transitory medium, which program code, when executed on a computer, executes a method of adjusting signal path gain in a hearing aid, comprising the steps of:

transforming an acoustic input signal into an electrical input signal;

generating an electrical output signal by amplifying said electrical input signal with a compressor gain provided by a compressor of said hearing aid depending on the level of said electrical input signal;

transforming said electrical output signal into an acoustic output signal;

calculating a level of autocorrelation of said current electrical input signal; and estimating a dynamic gain limit based on said calculated level of autocorrelation and the instantaneous compressor gain level for controlling said compressor gain.

21. The hearing aid according to claim 1, wherein said acoustic loop gain estimator is adapted to further adjust said dynamic gain limit by subtracting a safety margin from said dynamic gain limit.

* * * * *